United States Patent
Austin

(10) Patent No.: US 8,006,382 B2
(45) Date of Patent: Aug. 30, 2011

(54) METHOD OF MANUFACTURING FLOW SELECTOR DISK FOR FLUID PRESSURE REGULATOR

(75) Inventor: Gary R. Austin, Euclid, OH (US)

(73) Assignee: SP Medical LLC, Cleveland, OH (US)

( * ) Notice: Subject to any disclaimer, the term of this patent is extended or adjusted under 35 U.S.C. 154(b) by 1016 days.

(21) Appl. No.: 11/856,601

(22) Filed: Sep. 17, 2007

(65) Prior Publication Data

US 2008/0083117 A1    Apr. 10, 2008

Related U.S. Application Data

(60) Provisional application No. 60/826,004, filed on Sep. 18, 2006.

(51) Int. Cl.
*B21C 37/30* (2006.01)
*B21D 51/16* (2006.01)
*F16K 17/00* (2006.01)

(52) U.S. Cl. ............... 29/890.09; 29/890.14; 72/370.23; 137/315.04

(58) Field of Classification Search ............... 29/890.09, 29/890.1, 890.14, 890.142; 72/370.24, 370.25, 72/370.23; 137/315.04
See application file for complete search history.

(56) References Cited

U.S. PATENT DOCUMENTS

| | | | |
|---|---|---|---|
| 3,814,093 A | 6/1974 | Gregory | |
| 6,116,242 A | 9/2000 | Frye et al. | |
| 6,394,088 B1 | 5/2002 | Frye et al. | |
| 6,752,152 B2 | 6/2004 | Gale et al. | |
| 7,444,991 B2 * | 11/2008 | Joseph | 123/467 |

FOREIGN PATENT DOCUMENTS

WO    9711734 A1    4/1997

* cited by examiner

*Primary Examiner* — David P Bryant
*Assistant Examiner* — Alexander P Taousakis
(74) *Attorney, Agent, or Firm* — Pearne & Gordon LLP

(57) ABSTRACT

A method of manufacturing flow selector disk for a fluid pressure regulator, including the steps of providing a plate having a first face and a second face, and forming at least one baseline orifice in the plate including a first diameter portion adjacent the first face and a second diameter portion adjacent the second face. The first and second diameter portions are spaced a distance from each other to form an annular ring therebetween. A central flow portion is formed through the baseline orifice that is in fluid communication with both of the first and second diameter portions. The central flow portion has a relatively smaller diameter than either of the first and second diameter portions. The method also includes the step of plastically deforming a portion of the annular ring adjacent the central flow portion to thereby reduce the diameter of the central flow portion.

20 Claims, 4 Drawing Sheets

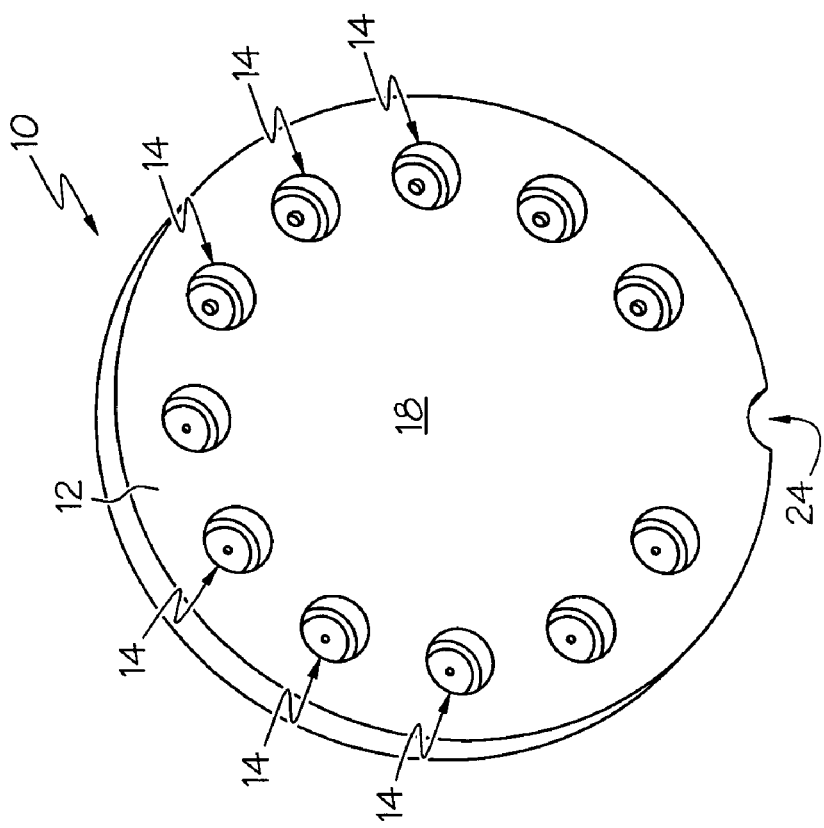
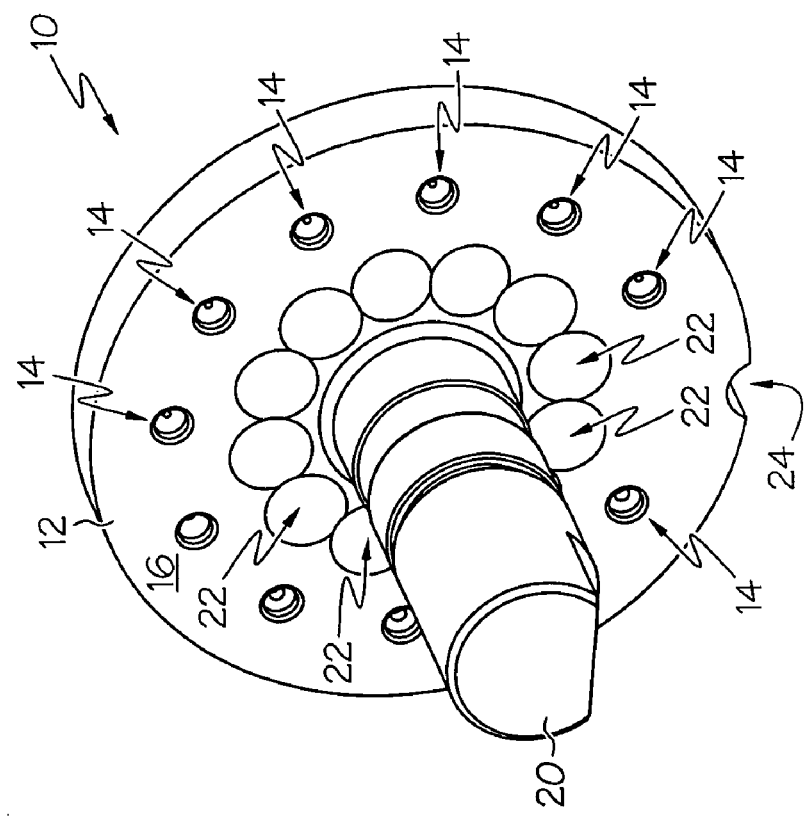

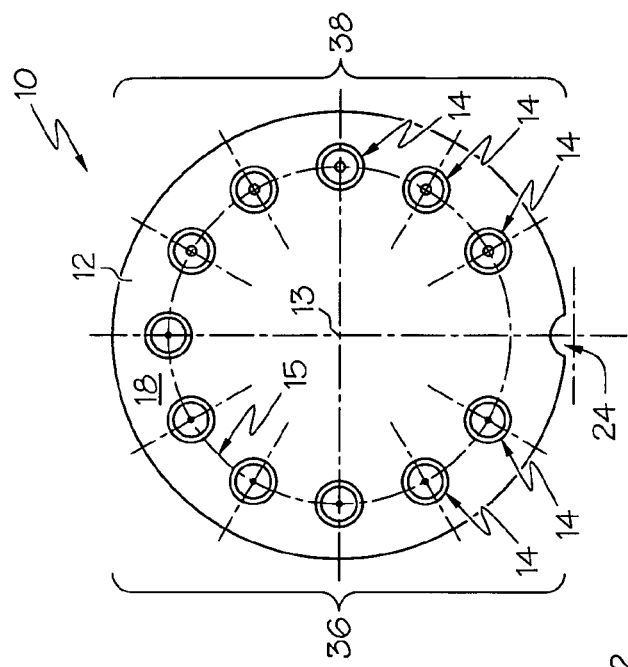
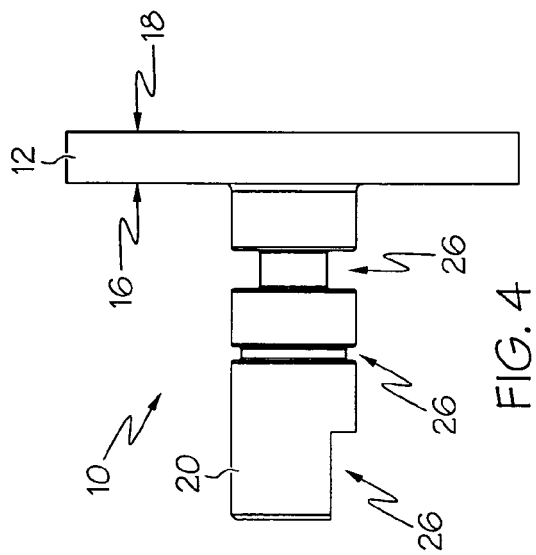
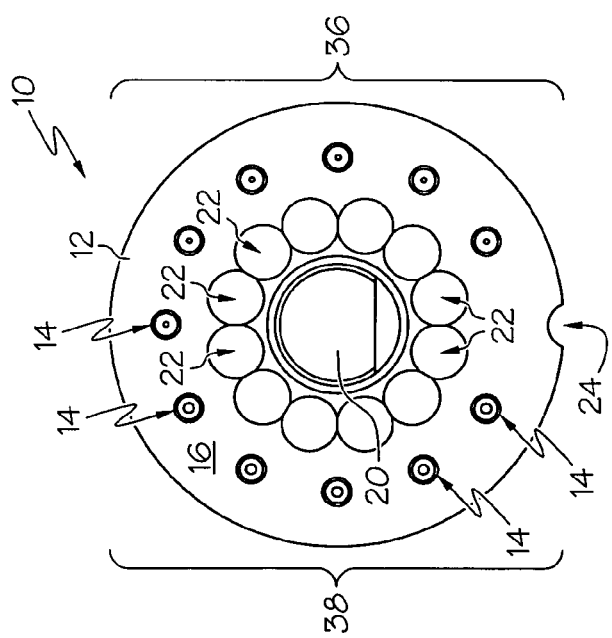
FIG. 5
FIG. 4
FIG. 3

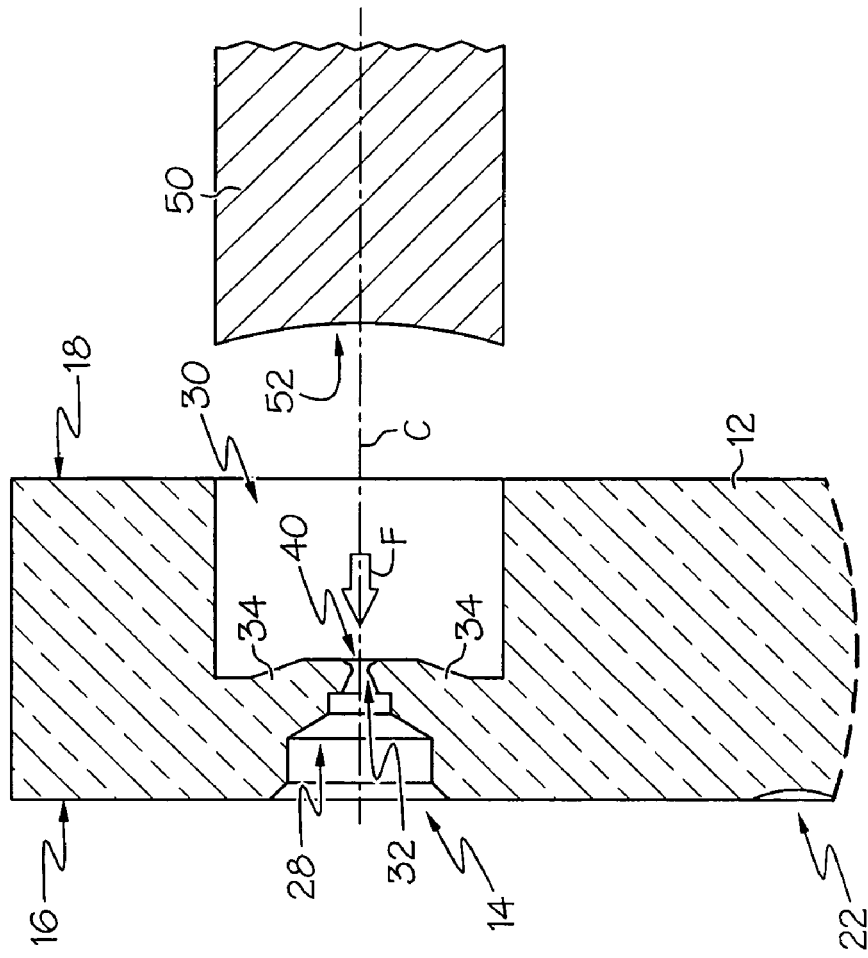
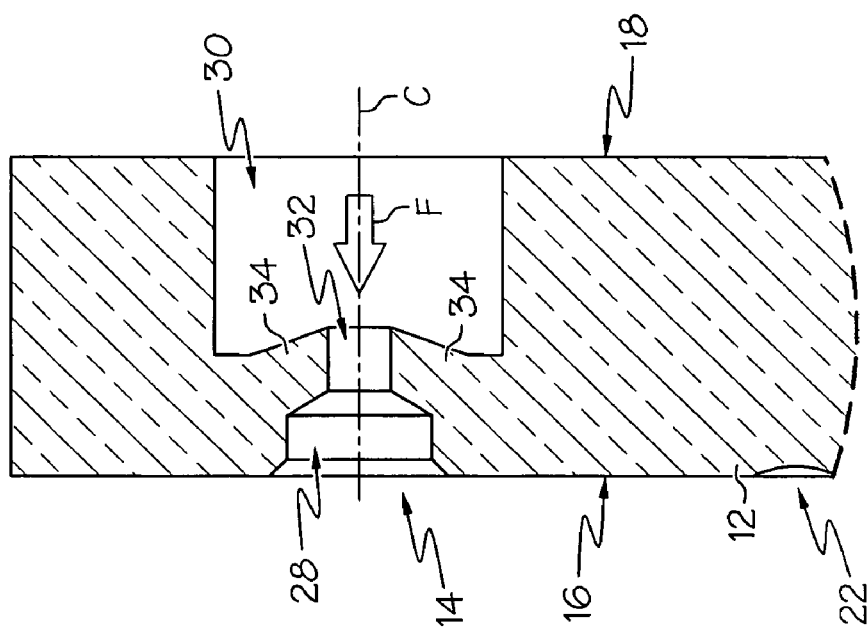

US 8,006,382 B2

METHOD OF MANUFACTURING FLOW SELECTOR DISK FOR FLUID PRESSURE REGULATOR

RELATED APPLICATIONS

This application claims the benefit of U.S. Provisional Application No. 60/826,004, filed Sep. 18, 2006, the entire disclosure of which is hereby incorporated herein by reference.

FIELD OF THE INVENTION

The present invention relates generally to a method of manufacturing an orifice, and more specifically to a method of manufacturing an orifice by way of a deformation operation.

BACKGROUND OF THE INVENTION

Conventionally, devices for the delivery of pressurized fluid flow, such as gas flow, can include an apparatus for regulating the flow rate of the pressurized fluid flow. In one example, the regulation apparatus can consist of a device, such as a plate or the like, having a plurality of variously sized orifices extending therethrough. Thus, a user can select a particular flow rate for delivery of the pressurized fluid by selecting one of the variously sized orifices for delivery of the fluid flow. Accordingly, the pressurized fluid will flow through the orifice at the desired flow rate.

The variously sized orifices can be formed using various conventional manufacturing processes. For example, where the regulation apparatus includes a plate, the variously sized orifices can be manufactured using operations, such as microdrilling, laser machining, punching, or the like. However, where the desired flow rates must be highly accurate and repeatable, such as in the field of medicine where very specific fluid flow rates must be achieved, the manufacturing process must be similarly accurate and repeatable (e.g., producing highly accurate dimensions and/or dimensional tolerances). While each of the aforementioned manufacturing processes are capable of producing a regulation device having orifices of specific sizes and accuracies, the processes can be expensive, time consuming, inefficient, and/or difficult to repeat effectively.

BRIEF SUMMARY OF THE INVENTION

The following presents a simplified summary of the invention in order to provide a basic understanding of some aspects of the invention. This summary is not an extensive overview of the invention. It is intended to identify neither key nor critical elements of the invention nor delineate the scope of the invention. Its sole purpose is to present some concepts of the invention in a simplified form as a prelude to the more detailed description that is presented later.

In accordance with an aspect of the present invention, a method of manufacturing flow selector disk for a fluid pressure regulator is provided. The method includes the steps of providing a plate having a first face and a second face, and forming at least one baseline orifice in the plate including a first diameter portion adjacent the first face and a second diameter portion adjacent the second face. The first and second diameter portions are spaced a distance from each other to form an annular ring therebetween. A central flow portion is formed through the baseline orifice that is in fluid communication with both of the first and second diameter portions. The central flow portion has a relatively smaller diameter than either of the first and second diameter portions. The method also includes the step of plastically deforming a portion of the annular ring adjacent the central flow portion to thereby reduce the diameter of the central flow portion.

BRIEF DESCRIPTION OF THE DRAWINGS

The foregoing and other aspects of the present invention will become apparent to those skilled in the art to which the present invention relates upon reading the following description with reference to the accompanying drawings, in which:

FIG. 1 illustrates a perspective view of an example regulation apparatus having variously sized orifices formed therethough using an example method of manufacturing in accordance with an aspect of the present invention;

FIG. 2 is similar to FIG. 1, but shows a rear perspective view of the example regulation apparatus;

FIG. 3 illustrates a top view of the example regulation apparatus of FIG. 1;

FIG. 4 is similar to FIG. 3, but shows a right side view;

FIG. 5 is similar to FIG. 3, but shows a bottom view;

FIG. 8 illustrates a detail view of FIG. 7; and

FIG. 9 is similar to FIG. 8, but shows an example target central diameter of an orifice in accordance with an aspect of the invention.

DESCRIPTION OF EXAMPLE EMBODIMENTS

Figure 7:
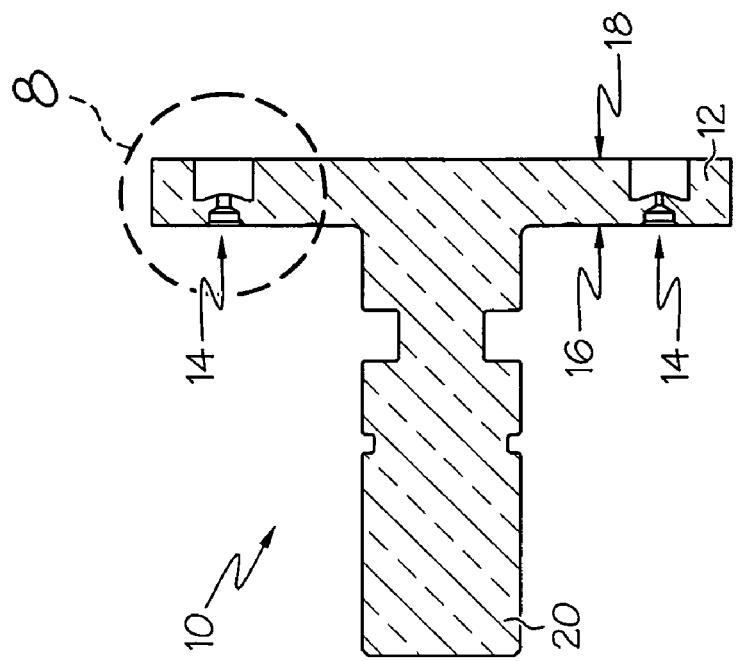
FIG. 7 is similar to FIG. 6, but shows a left side view with a sectional view along line 7-7 of FIG. 6.

Example embodiments that incorporate one or more aspects of the present invention are described and illustrated in the drawings. These illustrated examples are not intended to be a limitation on the present invention. For example, one or more aspects of the present invention can be utilized in other embodiments and even other types of devices. Moreover, certain terminology is used herein for convenience only and is not to be taken as a limitation on the present invention. Still further, in the drawings, the same reference numerals are employed for designating the same elements.

Turning to the shown example of FIG. 1, an example regulation apparatus 10 is shown in accordance with one aspect of the invention. In one example, the regulation apparatus 10 can be used to regulate the flow rate of a pressurized fluid flow, such as a gas, through a fluid delivery device (not shown). It is to be appreciated that while this discussion focuses on the delivery of a pressurized gas, the method of manufacture can be utilized with devices for the delivery of various fluids, including liquids, gas/liquid mixtures, gels, or the like. Additionally, the regulation apparatus 10 can include various generally rigid materials, such as metals, plastics, or the like, and can even include plastically deformable materials. In one example, the apparatus 10 can include brass or brass alloys, though various other materials are also contemplated.

As shown in FIGS. 1-2, the regulation apparatus 10 can include a plate 12 having a plurality of orifices 14 formed therethrough. As shown, the plate 12 has a generally circular geometry, though it can include various other geometries, such as square, rectangular, triangular, curved, elliptical, polygonal, random, etc. The orifices 14 extend through the plate 12 from a first face 16 to a second face 18. As will be discussed more fully herein, the orifices 14 can include various geometries (e.g., various diameters, counterbores, etc.). In one example, the orifices 14 can include a relatively smaller diameter adjacent the first face 16, and a relatively larger diameter adjacent the second face 18. The orifices 14 can be arranged in various manners, including various patterns, arrays, or even randomly. In one example, as shown in FIG. 5, each orifice 14 can be radially spaced a generally equal distance 15 from a point, such as a center point 13 of the plate 12. Of course, the various orifices 14 can also be arranged in various other manners. Additionally, it is to be appreciated that the method of manufacture discussed herein can be used to manufacture orifices through various other components aside from a plate.

Turning now to FIGS. 3-5, the example regulation device 10 can include various other features, such as a central shaft 20 for connection to a selection device (e.g., a handle or the like, not shown) for selective operation by a user, automated machine, or the like. In another example, the device 10 can include one or more of positional detents 22 corresponding to the selection of a particular orifice 14. As shown, the positional detents 22 can have a generally curved geometry for mating operation with a resiliently biased element, such as a resiliently biased plunger, ball, etc. In addition or alternatively, the number of detents 22 can be equal to, or even greater than, the number of corresponding orifices 14. For example, as shown, the device 10 can include twelve detents 22 and eleven orifices 14. Thus, the detents 22 can indicate selection of one of the orifices 14, and can even indicate the absence of an orifice (e.g., selection of a dead or no-flow position). In yet another example, the device can include one or more stops 24 adapted to inhibit movement (e.g., rotation) of the plate 12 at particular positions. It is to be appreciated that the various elements can also include various other components and/or features 26 (e.g., handle connection points, seal rings, bearing pockets, etc.) for use with various fluid delivery devices (not shown) and/or supporting structure thereof.

Figure 6:
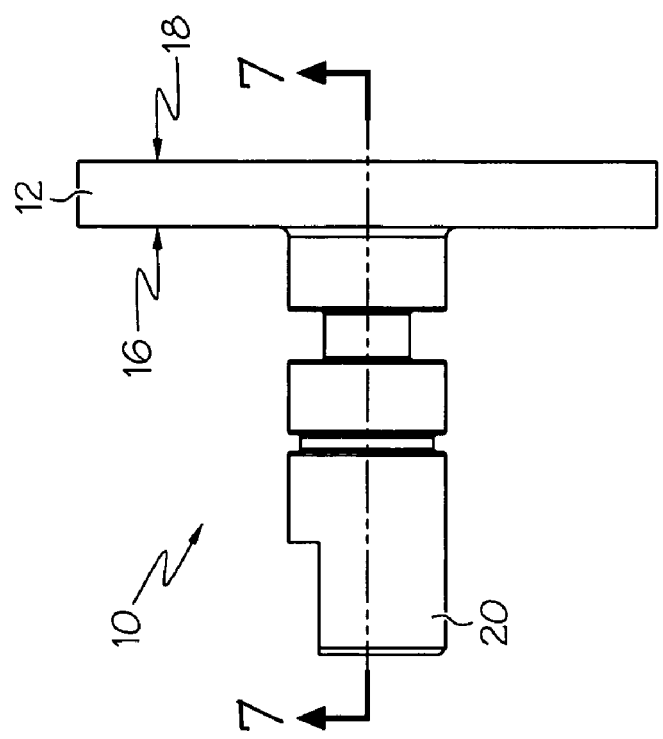
FIG. 6 is similar to FIG. 4, but shows a rotated view with section line 7-7 extending therethough.

Turning now to FIGS. 6-7, a sectional view of the example regulation device 10 along line 7-7 shows further details of the plate 12. As shown, the geometry of each orifice 14 can vary along its extent through the plate 12 from the first surface 16 to the second surface 18. Though the following discussion will focus on a generally round orifice 14 having one or more diameters, it is to be appreciated that some or all of the orifices 14 can also have various other geometries with various dimensions.

Turning now to the example shown in FIG. 8, an example orifice 14 is illustrated that can include various diameters. As shown, the orifice 14 can include a relatively smaller diameter 28 adjacent the first surface 16, a central flow diameter 32, and a relatively larger diameter 30 adjacent the second surface 18. Of course, though not shown, an orifice 14 can include only one of the relatively smaller diameter 28 or the relatively larger diameter 30 (e.g., one of the faces 16, 18 can remain generally flush and be penetrated by only the central flow diameter 32). It is to be appreciated that the desired flow rate for delivery of a fluid will be generally limited by the most restrictive portion (e.g., the most restrictive diameter) of the orifice 14. Thus, as shown, the desired flow rate will be generally limited by the diameter of the central flow diameter 32.

Both the relatively smaller and relatively larger diameter 28, portions can include various other features. For example, as shown, the relatively smaller diameter 28 portion can include a countersink feature, while the relatively larger diameter 30 portion can include counter-bore feature, though either portion 28, 30 can include various features. In another example, either or both of the relatively smaller and relatively larger diameter 28, 30 portions can include various features for engagement with flow direction devices (not shown) of a fluid delivery apparatus (e.g., mating portions, sealing portions, locking portions, etc., not shown) for handling and/or facilitating the fluid flow into and out of the regulation device 10. It is to be appreciated that the relatively smaller diameter 28, central flow diameter 32, and relatively larger diameter 30 can all be formed using various manufacturing processes, including drilling, boring, counter-sinking, counter-boring, reaming, stamping, forging, punching, molding, casting, etc.

For each orifice 14, the relatively smaller diameter 28, the central flow diameter 32, and the relatively larger diameter 30 can all be generally coaxial (or even concentric) along centerline C. Thus, the manufacturing operations (e.g., countersinking, counter-boring, etc.) forming the relatively smaller diameter 28 portion on one side of the central flow diameter 32, along with the formation of the relatively larger diameter 30 portion disposed on the other side of the central flow diameter 32, can create a tapered annular ring 34 that is similarly disposed generally coaxial to the central flow diameter 32. As shown, depending upon the various dimensions of the relatively smaller and larger diameters 28, 30, the tapered annular ring 34 portion can have a thickness (e.g., including a static thickness or a varying thickness) generally less than the nominal thickness of the plate 12. Turning briefly to FIG. 8, various example details of an orifice 14 are shown. It is to be appreciated that the wall angle of the annular ring 34 can vary from one side to the other (e.g., approximately 118° on the relatively smaller diameter 28 side versus approximately 140° on the relatively larger diameter side 32, as shown, though various other dimensions are also contemplated). It can be beneficial to have similar wall angles for the annular ring 34, such as parallel wall angles, though it can also be beneficial to have generally different wall angles (e.g., 118° versus a flat 180°), as will be described more fully herein.

Turning briefly back to FIGS. 3 and 5, an example method of forming the orifices 14, including the central flow diameter 32 portion, will now be described. First, the method includes the step of forming a baseline orifice through the plate 12. The relatively smaller diameter 28, central flow diameter 32, and relatively larger diameter 30 can be manufactured to be generally coaxial using various operations, including drilling, boring, counter-sinking, counter-boring, reaming, stamping, forging, punching, molding, casting, etc. Additionally, the central flow diameter 32 can be formed having a nominal diameter that is generally larger than the desired, target central diameter 40. For example, the central flow diameter 32 can be initially formed to an oversize condition with moderate tolerances.

Thus, in order to simplify manufacturing, one or more sets of similar baseline orifices 14 can be formed through the plate 12. In the shown example, the plate 12 includes two sets of baseline orifices 14, a first baseline set 36 (i.e., shown generally on the right-hand side in FIG. 3) and a second baseline set 38 (i.e., shown generally on the left-hand side in FIG. 3). The first baseline set 36 is shown having a relatively smaller first baseline central diameter while the second baseline set 38 is shown having a relatively larger, second baseline diameter. In one example, the relatively smaller first baseline central diameter can be 0.010 inches, while the relatively larger, second baseline diameter can be 0.020 inches. It is to be appreciated that the various dimensional values described herein are intended to only provide examples, and that various other dimensions can be used. It is further to be appreciated that various numbers of baseline orifices 14 can be arranged in various patterns, or even randomly, about the plate 12. Of course, more than two sets of baseline orifices 14 can be used.

Next, the method includes the step of forming the target central diameter 40 for each baseline orifice 14. As can be appreciated, because the regulation device 10 is configured to selectively provide various fluid flow rates, each target central diameter 40 can correspond to a particular, target central diameter. For example, the target central diameters 40 can include, in inches, 0.0047, 0.0067, 0.0079, 0.0088, 0.0103, 0.011, 0.0133, 0.0148, 0.0159, 0.0173, 0.0185, and/or various other diameters. Thus, the target central diameters that are less than the diameter of the first baseline set 36 (e.g. target diameters 0.0047 through 0.0088 that are less than the nominal diameter of 0.010) can be formed therewith, while the remaining target central diameters can be formed from the second baseline set 38 (e.g., target diameters 0.0103 through 0.0185 that are less than the nominal diameter of 0.020).

In one example, the step of forming each target central diameter 40 can include the step of plastically deforming the tapered annular ring 34 so as to reduce a portion of the diameter of the central flow diameter 32 portion. The tapered annular ring 34 can be plastically deformed by application of a force F applied to the annular ring 34 generally along the centerline C and in the direction from the second face 18 towards the first face 16. The force F can be applied to the annular ring 34 in various manners, as will be described herein.

For example, as shown in FIG. 9, the plate 12 can be secured from movement (e.g., clamped) and a plunger 50 or other force application element (not shown) can have an pressing surface 52 that is mechanically pressed against the tapered annular ring 34 to apply the force F. In one example, the plunger can have a geometry generally similar to that of the interior of the relatively larger diameter 30 (e.g., a plunger having a generally concave pressing surface 52). The application of the force F to the tapered annular ring 34 can cause plastic deformation of the annular ring 34 to thereby cause a portion of the central flow diameter 32 to be reduced in size. The force F can be applied until the central flow diameter 32 portion is approximately or exactly equal to the target central diameter 40.

It is to be appreciated that the force F can be applied in various other manners. For example, the plunger can include various other geometries, including a generally flat pressing surface, convex pressing surface, conical pressing surface, pyramidal pressing surface, etc. It is further to be appreciated that the force F could be applied from various other directions.

Thus, the step of forming each target central diameter 40 can including a swaging operation or other cold-working operation. However, it is to be appreciated that because of the small size and desired accuracy of the final hole diameters, it can be beneficial to provide a relatively slower application of pressure to the tapered annular ring 34 as opposed to a conventional swaging process that can include a repetitive, quick striking operation (e.g., a hammering operation or the like). However, it is conceivable that a quick striking operation could be used. Additionally, the forming process can be performed manually, or can be partially or even wholly automated.

As stated previously, the desired flow rate for delivery of a fluid will be generally limited by the most restrictive diameter of the orifice 14. Thus, the desired flow rate of a fluid will be generally limited by the target central diameter 40 that results from the plastic deformation forming operation. As such, it is to be appreciated that the central flow diameter 32 portion is not required to have a uniform diameter extending therethrough, nor does the generally geometry have to be generally uniform. Indeed, the central flow diameter 32 portion can have a non-circular (e.g., generally oblong or other non-uniform geometry), so long as the desired flow rate for delivery of the fluid is achieved.

Thus, the method can further include the step of verifying the flow rate of a target fluid through the target central diameter 40. In one example, a particular amount of the target fluid (e.g., a gas, such as air) can be provided through the relatively smaller diameter 28 portion, pass through the deformed central flow diameter 32 and received at the relatively larger diameter 30 portion by a fluid flow sensor (e.g., a mass air sensor or the like). The fluid flow sensor can determine, through various methods (e.g., including methods that may or may not account for and/or measure the various physical properties of the fluid and the appropriate environmental variables), the actual fluid flow rate through the deformed central flow diameter 32. Thus, if the measured fluid flow rate is equal to the desired flow rate, the deformation process is finished. If the measured fluid flow rate is not equal to the desired flow rate, the deformation process can be repeated (e.g., a further application of the force F, or even a modified force F) and the flow rate retested. Finally, once a particular target central diameter 40 is obtained for a specific orifice 14, the process can be repeated to form the next orifice 14. Of course, such measurement and/or calibration can also be automated.

Additionally, the measurement process can be performed manually, or can partially or even wholly automated. In one example, the plunger (not shown) can apply the force F, and then can be moved a small distance (e.g., 0.060 inches) away from the tapered annular ring 34. The fluid flow measurement (e.g., gas flow measurement) can be performed around the plunger (e.g., through the use of a chamber (not shown) formed with or surrounding the plunger). Then, if further application of the force F is required, the plunger can be moved back into contact with the tapered annular ring 34 and the deformation process continued until the desired flow rate is achieved.

It is to be appreciated that various other methods can also be used to verify the target central diameter 40. Although the flow rate of the fluid can be used, a measurement of the target central diameter 40 can also be used to infer the desired flow rate. For example, the target central diameter 40 could be measured by a suitable measuring instrument (e.g., micrometer or the like) and, knowing the variables of fluid flow (e.g., variable of gas flow, environmental variables, etc.), the flow rate of the specific fluid can be determined, such as through calculation or by a look-up table or chart. Of course, the verification can also be partially or wholly automated.

It is also to be appreciated that the example method described herein could also be utilized to enlarge the nominal diameter of the central flow diameter 32. For example, a plunger (not shown) could apply a force (not shown) against the tapered annular ring 34 from the direction of the first face 16 towards the second face 18 to thereby enlarge the central flow diameter 32. Of course, such an enlarged diameter could permit an increased fluid flow therethrough. The various methods described herein could also subsequently be used to verify the correct target diameter and/or fluid flow.

The invention has been described with reference to the example embodiments described above. Modifications and alterations will occur to others upon a reading and understanding of this specification. Examples embodiments incorporating one or more aspects of the invention are intended to include all such modifications and alterations insofar as they come within the scope of the appended claims.

What is claimed is:

1. A method of manufacturing a flow selector disk for a fluid pressure regulator, including the steps of:

providing a plate having a first face and a second face;
forming at least one baseline orifice in the plate including a first diameter portion adjacent the first face and a second diameter portion adjacent the second face, the first and second diameter portions being spaced a distance from each other to form an annular ring therebetween;
forming a central flow portion through the at least one baseline orifice that is in fluid communication with both of the first and second diameter portions, the central flow portion having a relatively smaller diameter than either of the first and second diameter portions; and
plastically deforming a portion of the annular ring adjacent the central flow portion to thereby reduce the diameter of the central flow portion.

2. The method of claim 1, further including the steps of providing a plunger having a pressing surface, and utilizing the pressing surface to plastically deform the annular ring.

3. The method of claim 2, wherein the central flow portion has a central axis, and wherein each of the first diameter portion and the second diameter portion are generally coaxial with the central axis.

4. The method of claim 3, wherein the pressing surface of the plunger is configured to apply a force to the annular ring along a force axis that is generally coaxial to the central flow axis.

5. The method of claim 2, wherein the pressing face includes a generally concave geometry.

6. The method of claim 1, further including the steps of
measuring an actual fluid flow rate of a target fluid through the central flow portion;
comparing the actual fluid flow rate of the target fluid through the central flow portion against an expected flow rate; and
altering the diameter of the central flow portion until the actual fluid flow rate of the target fluid is approximately equal to the expected flow rate.

7. The method of claim 6, further including the steps of providing a plunger having a pressing surface, and utilizing the pressing surface to plastically deform the annular ring, wherein the plunger is configured to facilitate the step of measuring the actual fluid flow rate of the target fluid through the central flow portion.

8. The method of claim 1, further including the step of providing the plate with a plurality of baseline orifices, wherein a first set of the baseline orifices include a first central flow portion each having a first diameter, and a second set of the baseline orifices include a second central flow portion each having a second diameter.

9. The method of claim 8, further including the step of plastically deforming at least one central flow portion of the first set towards a first target diameter within a first diameter range, and plastically deforming at least one central flow portion of the second set towards a second target diameter within a second diameter range.

10. The method of claim 9, wherein the first diameter range has a value less than 0.25 millimeters (0.010 inches), and wherein the second diameter range has a value approximately equal to or greater than 0.25 millimeters (0.010 inches).

11. The method of claim 1, further including the steps of providing the plate with a plurality of baseline orifices, and providing the plate with a plurality of positional detents, at least one of the plurality of positional detent corresponding to at least one of the plurality of baseline orifices.

12. A method of manufacturing a flow selector disk for a fluid pressure regulator, including the steps of:
providing a plate having a first face, a second face, and a thickness dimension;
forming at least one baseline orifice in the plate including a central flow portion extending through the plate between the first and second faces and along a central flow axis, the at least one baseline orifice including a geometry defining a cross-sectional dimension;
forming a first aperture portion in the plate adjacent to the first face and along an axis generally coaxial with the central flow axis, the first aperture portion being in fluid communication with the central flow portion and having a relatively larger cross-sectional dimension than the cross-sectional dimension of the central flow portion, the first aperture portion extending into the plate a longitudinal distance less than the thickness dimension of the plate so as to create an annular ring at the interface of the first aperture portion and the central flow portion; and
plastically deforming a portion of the annular ring adjacent the central flow portion to thereby reduce the cross-sectional dimension of the central flow portion.

13. The method of claim 12, further including the steps of:
providing a plunger having a pressing surface, the plunger being adapted to be inserted into the first aperture portion;
inserting the plunger into the first aperture portion to locate the pressing face in abutment with at least a portion of the annular ring; and
applying a force to the plunger along a force axis generally coaxial with the central flow axis to thereby plastically deform the annular ring to reduce the cross-sectional dimension of the central flow portion.

14. The method of claim 12, further including the steps of:
measuring an actual fluid flow rate of a target fluid through the central flow portion;
comparing the actual fluid flow rate of the target fluid through the central flow portion against an expected flow rate; and
altering the cross-sectional dimension of the central flow portion until the actual fluid flow rate of the target fluid is approximately equal to the expected flow rate.

15. The method of claim 12, further including the step of forming a second aperture portion in the plate adjacent to the second face and along an axis generally coaxial with the central flow axis, the second aperture portion being in fluid communication with the central flow portion and having a relatively larger cross-sectional dimension than the cross-sectional dimension of the central flow portion, the second diameter portion being spaced a distance from the first diameter portion to form the annular ring therebetween.

16. The method of claim 12, further including the steps of:
providing the plate with a plurality of first baseline orifices each having a first central flow diameter;
providing the plate with a plurality of second baseline orifices each having a second central flow diameter;
plastically deforming at least one of the plurality of first baseline orifices to thereby reduce the respective first central flow diameter to have a value less than 0.25 millimeters (0.010 inches); and
plastically deforming at least one of the plurality of second baseline orifices to thereby reduce to thereby reduce the respective second central flow diameter to have a value approximately equal to or greater than 0.25 millimeters (0.010 inches).

17. The method of claim 12, further including the steps of providing the plate with a plurality of baseline orifices, and providing the plate with a plurality of positional detents, at least one of the plurality of positional detents corresponding to at least one of the plurality of baseline orifices.

18. A method of manufacturing a flow selector disk for a fluid pressure regulator, including the steps of:
providing a plate having a first face and a second face;
forming at least one baseline orifice in the plate including a central flow portion extending through the plate and along a central flow axis;
forming a first diameter portion in the plate adjacent the first face and generally coaxial with the central flow axis;
forming a second diameter portion in the plate adjacent the second face and generally coaxial with the central flow axis, the second diameter portion being spaced a distance from the first diameter portion so as to form an annular ring therebetween;
providing a plunger having a pressing surface, the plunger being adapted to be inserted into at least one of the first and second diameter portions;
inserting the plunger into the second diameter portion to locate the pressing face in abutment with at least a portion of the annular ring;
applying a force to the plunger along a force axis generally coaxial with the central flow axis; and
plastically deforming a portion of the annular ring adjacent the central flow portion to thereby reduce the diameter of the central flow portion.

19. The method of claim 18, further including the steps of:
measuring an actual fluid flow rate of a target fluid through the central flow portion;
comparing the actual fluid flow rate of the target fluid through the central flow portion against an expected flow rate; and
altering the cross-sectional dimension of the central flow portion until the actual fluid flow rate of the target fluid is approximately equal to the expected flow rate.

20. The method of claim 18, further including the steps of:
providing the plate with a plurality of first baseline orifices each having a first central flow diameter;
providing the plate with a plurality of second baseline orifices each having a second central flow diameter;
plastically deforming at least one of the plurality of first baseline orifices to thereby reduce the respective first central flow diameter to have a value less than 0.25 millimeters (0.010 inches); and
plastically deforming at least one of the plurality of second baseline orifices to thereby reduce to thereby reduce the respective second central flow diameter to have a value approximately equal to or greater than 0.25 millimeters (0.010 inches).

\* \* \* \* \*